N. I. DONALDSON.

Inhalers.

No. 5,491. Reissued July 15, 1873.

Witnesses.
E. A. Bates.
Chas. B. Stule

Inventor.
N. I. Donaldson,
Chipman & Souther & Co.,
attys.

AM. PHOTO-LITHOGRAPHIC CO. N.Y. (OSBORNE'S PROCESS)

UNITED STATES PATENT OFFICE.

NILES I. DONALDSON, OF WORCESTER, MASSACHUSETTS.

IMPROVEMENT IN INHALERS.

Specification forming part of Letters Patent No. 134,861, dated January 14, 1873; reissue No. 5,491, dated July 15, 1873; application filed May 31, 1873.

*To all whom it may concern:*

Be it known that I, NILES I. DONALDSON, of the city and county of Worcester and Commonwealth of Massachusetts, have invented certain new and useful Improvements in Medical Inhalers; and I do hereby declare that the following is a full, clear, and exact description of the construction and operation of the same, reference being had to the annexed drawings forming a part of this specification and to the letters and figures of reference marked thereon.

Figure 1:
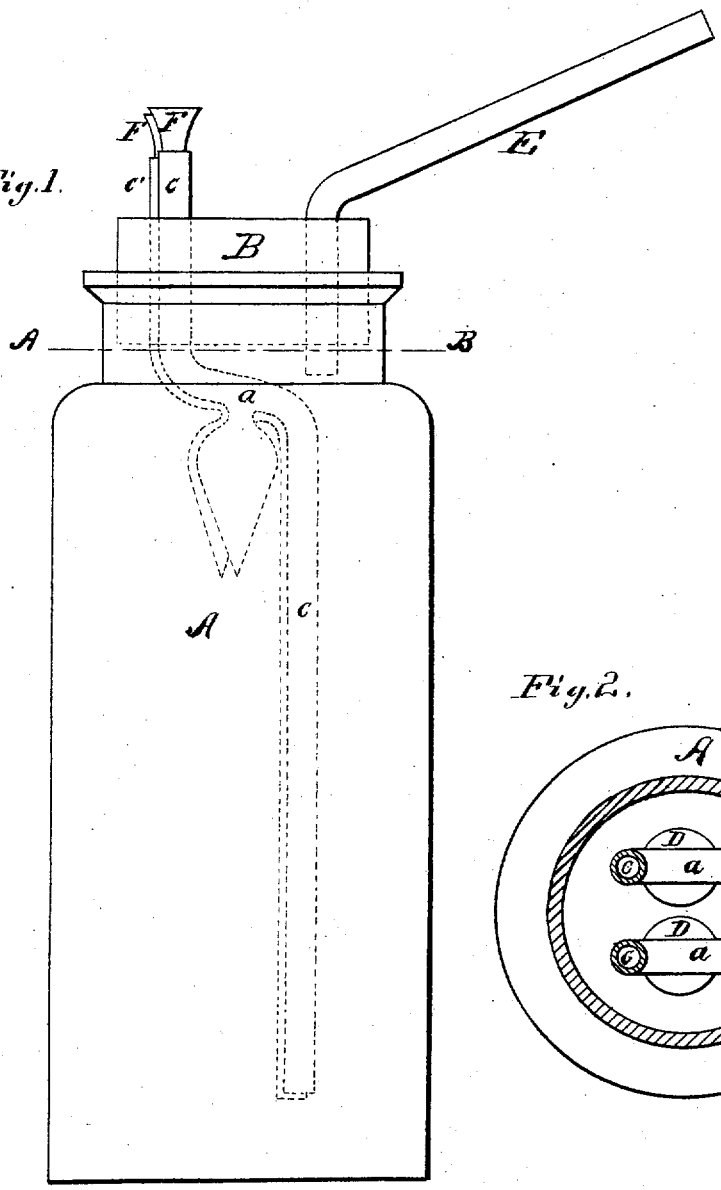
Figure 3:
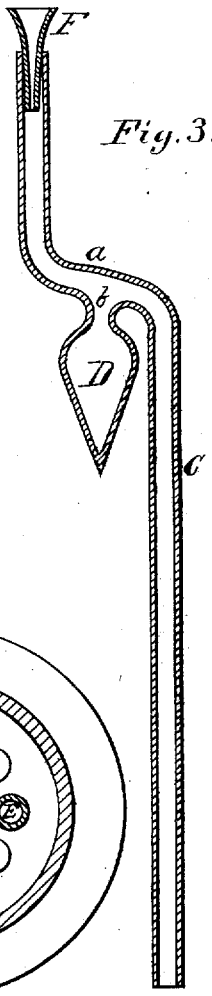
Figure 2:
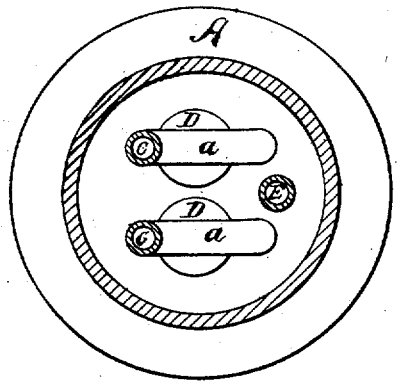

Referring to the drawings, Figure 1 represents a side view of my improved inhaler. Fig. 2 represents a horizontal section of the same at line A B, Fig. 1. Fig. 3 represents a central section through one of the tubes.

The object of this invention is to provide an inhaler that is more compact in form and more convenient to use than those heretofore in use; and to that end the nature of my invention consists, first, in a peculiarly-constructed bulbed inlet-tube, as hereinafter set forth; and, second, in the combination and relative arrangement of the several parts of the apparatus, in the manner set forth, to produce a simple, effective, and durable inhaler.

In the drawing, the part marked A represents the main receptacle, which, in the present instance, is a small glass jar fitted with a cork stopper, B. C C′ indicate the inlet-tubes, which I make of the peculiar form shown. These tubes are bent or curved in such a manner that a portion of the tubing at *a* will be nearly in a horizontal position, and to the lower side of the part *a* is attached a hollow bulb, D, for containing the medicinal liquid. The bulb D communicates with the tube by a passage, *b*, through the attachment, the tube and bulb being blown from glass in a single piece. The upper portion of the tubes C C′ are arranged through the stopper B, while their lower ends extend nearly to the bottom of the receptacle A, the bulbs D being completely inclosed within the interior of said receptacle A, as illustrated. E indicates the draft-tube, which is arranged through the stopper B from the upper part of the receptacle A and projects outward in an inclined position, as shown. F F indicate small funnels arranged in the upper ends of the tubes C C′, through which to pour the liquids into the bulbs D. These funnels also serve as valves to nearly close the mouth of the tubes, so that when inhaling through the draft-tube E the air is partially exhausted within the receptacle and tubes C C′, thus causing the vapor to rise more rapidly from the liquids within the bulbs D. The bulbs D are to be charged with the liquids usually employed for producing medicated vapors—viz., hydrochloric acid in one, and ammonia in the other—while the main receptacle is to be filled about one-half full of water, medicated or otherwise, as preferred. As the air passes into the interior, through the tubes C C′, it becomes charged with the vapors arising from the liquids in the respective bulbs. These vapors are purified as they bubble up through the water, and, mingling in the upper part of the receptacle, pass to the patient through the draft-tube E.

The inhalers may be made with one or both of the inlet-tubes, as desired. When but one inlet-tube is used the alkali is placed in the main receptacle A with the water, the acid being introduced into the bulb of the inlet-tube.

Among the advantages obtained by constructing the inhaler in accordance with my invention, as shown and described, may be mentioned the following: The peculiar form of the inlet-tube and bulb is such that the air passes over instead of through the acid or other liquid in the bulb; consequently the vapor is less harsh than it otherwise would be. The bulbs and tubes being placed in the interior of the receptacle render the apparatus compact and convenient for use, and the bulbs are not liable to be broken or the tubes injured, while the form of the bulb is such that the liquid is not liable to overflow by the agitation caused by handling the apparatus. It will also be observed that the stopper B, bulbed tubes C C′, and draft-tube E are all so arranged as to fit into a single opening; consequently an ordinary small jar or wide-mouthed bottle can be used for the main receptacle A, thus rendering it unnecessary to have the receptacles made specially for the purpose. This greatly reduces the cost of the apparatus, and, in case of accident to the receptacle, obviates much inconvenience to the person using in sending for and procuring a new receptacle.

What I claim as new, and desire to secure by Letters Patent, is—

1. The combination, with the receptacle in an inhaling apparatus, of the peculiarly-constructed inlet-tube C provided with a bulb, D, upon the lower side of the bent or horizontal portion *a* of the tube, substantially as set forth.

2. The combination, with the inlet-tubes C C′, of the funnels or valves F, substantially as and for the purpose set forth.

3. An inhaling apparatus, consisting of a main receptacle, A, having a single opening provided with a stopper, B, inlet-tube or tubes C, liquid bulb or bulbs D upon the lower side of the bent or horizontal portion of the tube which is within the main receptacle and draft-tube E, substantially as set forth.

4. The peculiarly-constructed inlet-tube C bent at *a*, as shown, and having the communicating bulb D blown on the lower side of the bent or horizontal portion of the tube, as and for the purposes specified.

In testimony that I claim the above I have hereunto subscribed my name in the presence of two witnesses.

N. I. DONALDSON. [L.S.]

Witnesses:
GEO. MCALEER,
I. C. BATES SMITH.